(12) United States Patent
Siepmann et al.

(10) Patent No.: US 7,330,262 B2
(45) Date of Patent: Feb. 12, 2008

(54) METHODS AND APPARATUS FOR DETERMINING THE CONTENT MATERIALS OF A LIQUID EMPLOYING A PISTON MOVABLE WITHIN A MEASURING CHAMBER

(75) Inventors: Friedrich W. Siepmann, Darmstadt (DE); Achim Gahr, Goldbach (DE)

(73) Assignee: Endress+Hauser Conducta Gesellschaft fur Mess - und Regeltechnik mbH+Co. KG, Gerlingen (DE)

( * ) Notice: Subject to any disclaimer, the term of this patent is extended or adjusted under 35 U.S.C. 154(b) by 244 days.

(21) Appl. No.: 10/503,806

(22) PCT Filed: Jan. 30, 2003

(86) PCT No.: PCT/EP03/00929

§ 371 (c)(1),
(2), (4) Date: Jan. 21, 2005

(87) PCT Pub. No.: WO03/067228

PCT Pub. Date: Aug. 14, 2003

(65) Prior Publication Data
US 2005/0117156 A1    Jun. 2, 2005

(30) Foreign Application Priority Data
Feb. 6, 2002 (DE) ................................ 102 04 963

(51) Int. Cl.
*G01N 21/00* (2006.01)
(52) U.S. Cl. ........................ 356/441; 356/432; 356/433; 356/440

(58) Field of Classification Search ................. 356/244, 356/246, 437, 442
See application file for complete search history.

(56) References Cited

U.S. PATENT DOCUMENTS

| | | | | | |
|---|---|---|---|---|---|
| 3,106,096 | A | * | 10/1963 | Broerman | 73/863.12 |
| 3,263,553 | A | * | 8/1966 | Baruch | 250/574 |
| 3,714,445 | A | * | 1/1973 | Blachere et al. | 250/576 |
| 4,021,120 | A | * | 5/1977 | Muller et al. | 356/442 |
| 4,194,391 | A | * | 3/1980 | Rosenberger | 73/61.69 |
| 4,280,913 | A | * | 7/1981 | Applegate et al. | 210/669 |
| 4,313,340 | A | * | 2/1982 | Schniewind | 73/61.69 |
| 4,641,969 | A | * | 2/1987 | Lundberg et al. | 356/343 |
| 4,774,417 | A | * | 9/1988 | Houpt | 250/574 |
| 4,908,676 | A | * | 3/1990 | Bedell et al. | 356/72 |

(Continued)

FOREIGN PATENT DOCUMENTS

AT    408 149    9/2001

(Continued)

*Primary Examiner*—Gregory J. Toatley, Jr.
*Assistant Examiner*—Jarreas Underwood
(74) *Attorney, Agent, or Firm*—Drinker Biddle & Reath LLP

(57) ABSTRACT

The contents of a liquid medium are determined using a light source and an optical detector, for example a spectrometer. A longitudinally displaceable piston sucks the medium into a cylindrical glass measuring chamber and evacuates the liquid from the chamber. At least one measuring beam is directed through the medium, and at least one reference beam is directed outside the medium. The piston has cleaning/sealing rings mounted on its outer periphery which rub against an inner surface of the glass measuring chamber as the piston travels, to clean the surface.

18 Claims, 3 Drawing Sheets

U.S. PATENT DOCUMENTS

| | | | |
|---|---|---|---|
| 5,610,706 A * | 3/1997 | Carroll et al. | 356/70 |
| 5,807,750 A * | 9/1998 | Baum et al. | 436/164 |
| 6,542,231 B1 * | 4/2003 | Garrett | 356/246 |
| 6,678,050 B2 * | 1/2004 | Pope et al. | 356/435 |

FOREIGN PATENT DOCUMENTS

| | | |
|---|---|---|
| DE | 33 40 570 | 5/1984 |
| DE | 32 48 070 | 6/1984 |
| EP | 0 459 846 | 12/1991 |
| EP | 1 013 326 | 6/2000 |
| EP | 0 634 645 | 7/2003 |
| GB | 2 134 253 | 8/1984 |
| WO | WO 97/21088 | 6/1997 |
| WO | WO 99/43621 | 9/1999 |
| WO | WO 01/46676 A2 | 6/2001 |

* cited by examiner

METHODS AND APPARATUS FOR DETERMINING THE CONTENT MATERIALS OF A LIQUID EMPLOYING A PISTON MOVABLE WITHIN A MEASURING CHAMBER

BACKGROUND

The invention relates to a method for determining the content materials of a liquid medium using a light source and an optical detector, for example a spectrometer, with at least one measuring beam and at least one reference beam, and whereby at least one measuring beam is directed through the medium that is to be analyzed and at least one reference beam is directed outside of the medium that is to be analyzed.

The probes, measuring in a photometric manner and which are used in the context of such methods, for the "in situ" use in order to determine the content materials of a liquid, for example of river water or of waste water, usually have a light source and an optical detector, for example a spectrometer, with at least one measuring beam and at least one reference beam, and whereby the light of the light source is fanned, if need be, and brought into focus in one essentially parallel beam by way of at least one optical lens.

Spectrometers featuring measuring and reference beams are known from DE 3 248 070-A1 and DE 3 340 570-A1; regarding "in situ" measurements from AT-A2167/99.

DE 3 248 070 A1 relates to an infrared analyzer with a beam that is divided and directed, on the one hand, through a measuring cuvette and, on the other hand, through a reference cuvette.

DE 3 340 570 A1 relates to a spectral photometer, which also provides for the division of the beam into a measuring beam and a reference beam, but here with a temporal offset by a rotating mirror. In this instance, a joint detector is envisioned for both beams. In order to ensure that both partial beams have the same wavelength, the frequency shift in the monochromer is only effected when no measurement occurs.

Both apparatuses are set up discretely, i.e. they are comprised of several units, that may, though, have a joint housing which, however, does not allow for the apparatus as a whole to be immersed into the fluid that is to be measured; but it is necessary to place any samples that are taken in the apparatus using the corresponding containers such as cuvettes, etc.

AT-A 2167/99 relates to a spectral probe for "in situ" measuring. With this probe the measuring beam is directed through a light-transparent window into the fluid that is to be examined and then, through another light-transparent window, redirected into the probe. The reference beam is only directed on the inside of the probe without passing through the windows that touch the fluid.

Also available are optical probes that are immersed in the fluid and that measure "in situ." But these probes do not work spectrometrically; instead their function is limited to only one wavelength or the integral of a wave range, and they measure the opacity of the fluid or the concentration of an individual special content material. The latter named methods are not able to examine the optical quality of the windows because the reference beams, insofar as they are available, run on the inside of the housing. But the optical quality of the windows has an influence that is quite essential relative to the quality of the measurement because, primarily when measuring waste water, window discolorations and bacterial growth cannot be avoided and even with mechanical cleanings, such as by means of window wipers, it is not possible to guarantee the optical quality of the window.

Moreover, with the aforementioned systems, it is not possible to separate content materials that are mechanically settable, such as activated sludge in the activated sludge lagoon of a water treatment plant, from waste water. Thus, settlement units must be arranged in series upstream of the systems in order to measure the activated sludge whereby, however, in particular the value of an "in situ" measurement is lost.

The need for "in situ" measurements of water types, in particular of river water, waste water and process waters in pipes, is increasing. Using spectral photometry, it is possible to measure characteristics, such as e.g. nitrate and the SAK (spectral absorption coefficients) directly. In combination with mathematical optimization methods that are available today, such as e.g. neuronal nets, it is possible to provide with a correspondingly qualified measuring technique sum parameters, such as e.g. TOC and CSB, as substitute parameters.

Thus, the object of the invention consists in configuring the method and the apparatus in such a way that measuring and reference beams have to pass through the same optical glasses, with the same opacities and contaminations, that a measuring chamber is created that will allow for the evacuation of settable materials from the area of the measuring and reference beams.

SUMMARY OF INVENTION

According to the invention, the object is achieved in that a longitudinally displaceable piston device, e.g., a piston or piston slide valve, sucks the medium that is to be analyzed into a measuring chamber and evacuates said medium from said chamber, and in that the piston or piston slide valve cleans the window in the optical beam path during its lifting motion.

The medium that is to be measured is sucked into a glass cylinder by means of the piston. The optical axis consisting of a light source, of at least one optical lens that brings the light into focus in an essentially parallel beam, of at least one optical lens that directs the light after it leaves the measuring medium to the entry point of a light guide or the inlet of a spectrometer or photo-detector, is arranged transversely relative to the cylinder axis. The cylinder axis is directed, for example, perpendicularly upwards. The optical axis and the axis of the measuring cylinder intersect, for example, at an angle of 90°.

According to the invention, at least one measuring beam is directed through the fluid that is to be analyzed and at least one reference beam is directed with a temporal offset through a piston or piston slide valve displacing the fluid. In this instance it is possible to use a collecting optic comprised of at least one lens that directs the beams to the contact point of a light guide or to the inlet of a photo-detector or the spectrometer, and whereby the piston displacing the fluid can serve as beam shutter that allows a part of the light rays of the beam to pass while shielding the rest.

Advantageously, it is envisioned that when the lower edge of the piston is congruent with the upper edge of the optical lenses the spectrometric measurement is carried out; the results of the reference beam and the results of the measuring beam for each wavelength or for individual ranges of the spectrum are calculated in accordance with the mathematical relation $E1 = L1 * E_{spez} + C$ $E2 = L2 * E_{spez} + C$ It can be envisioned that the spectrometer is configured as a probe, that the inlet of the measuring cylinder is immersed into the medium to be analyzed in the base region of the probe, that a piston empties into the measurement cylinder while simultaneously cleaning the inside walls of the measuring cylinder with its sealing and cleaning lips, that the piston for filling the measuring cylinder moves upward, that, provided the reference bore is congruent with the optical axis, the reference measurement is carried out, and that, following the release of the optical axis, the measurement is conducted.

In an advantageous embodiment, the piston with sealing and cleaning lips has at least one through-bore in the cylinder center arranged transversely relative to the cylinder axis for a reference beam. This through-bore axis is located parallel relative to the optical axis. The measuring plane is released when the piston assumes a position above the optical lenses.

The length of the medium-filled measuring area, as measured along the optical axis, corresponds to the length of the measuring path of the measuring beam. The length of the measuring path is determined depending on the substances that are to be measured and the necessary measuring accuracy. For very strongly absorbing substances, the path length is typically approximately 2-3 mm, for very minimally absorbing substances, the path length is 50-100 mm and more. From a technical perspective a path length of approximately 5-20 mm is considered sufficient for achieving measuring accuracy with various media.

The piston through-bore reduces the measuring beam to the necessary surface dimension of the reference beam. The surface ratio between measuring beam and reference beam is 1 to 5, depending on the measuring medium. Therefore, according to the invention, it is possible for the piston to contain additional reference bores arranged on top of each other and graduated in terms of their diameters, allowing the computer to automatically select the suitable reference bore.

An improvement of the invention therefore envisions that at least one additional reference beam that is different from the diameter of the first reference beam is measured, and then the computer determines the optimal reference beam.

At least in the area of the lenses, the measuring cylinder if preferably manufactured from UV-resistant and UV-transparent quartz glass. It is advantageous to manufacture the cylinder in its entirety from a suitable glass. This way, it is possible to avoid any transitions between glass and other materials that may cause interferences.

According to the invention, the receiving unit of the optical plane, comprised of a light source, of at least one optical lens that brings the light into focus in an essentially parallel beam, and at least one optical lens that directs the light after it leaves the measuring medium to the entry point of a light guide or the inlet of a spectrometer or photo-detector, is manufactured of a UV-resistant assembly block preferably consisting of round bar material. This way the components are fixed in place in terms of their axes. Correspondingly, lamp, light guide and lenses can be displaceably installed or mounted as fixed in place in the light axis for the purpose of effecting fine alignment. The receiving unit of the optical plane is provided with a through-bore for the measuring cylinder. This causes the optical axis and the measuring cylinder axis to be fixed in their respective positions. The axes intersect at an angle of 90°.

In the configuration of the method according to the invention for measuring in the lagoon of a water treatment plant, the piston is pulled upward at such slow speed that the activated sludge in the lower area of the measuring cylinder generates a suspension filter of activated sludge, which is why in the area of the optical axis a medium becomes collected that is, for the most part, free of solid matter, and that the state of the, for the most part, absence of solid matter is checked by way of the optical measurement. But it is also possible to pull the piston upward with a speed that is larger than the settling speed of the activated sludge. The filling speed is preferably in the range of 0.5 and 2.0 cm per second. In this case, the measuring medium is allowed a dwell time for the settling until the beginning of the photometric measurement. In the last named filling state, when the piston position above the optical axis is reached, the opacity level of the medium is measured in preset second intervals. After a preset purification level has been reached, the computer automatically initiates the photometric measurement.

In particular, it can be envisioned that when measuring activated sludge the piston for filling the measuring cylinder is pulled upward at such a speed that de-blending of sludge and medium cannot occur and that, when the lower edge of the piston is congruent with the upper edge of the optical lenses, the settling level of the sludge-medium blend is optically measured at second-intervals which are to be preset, and that once a medium is achieved in the optical axis that is, for the most part, free of solid matter, the actual photometric measurement is started, and that the measured data obtained during the measuring of the settling level are evaluated for the determination of the so-called sludge dry solid matter, the so-called sludge volume and the so-called sludge index.

It is possible to envision that the light of the light source is fanned and, using at least one optical lens, brought into focus in an essentially parallel beam.

An apparatus for implementing the method with a light source, a photo detector, for example a spectrometer, and at least one optical lens as collective optic is characterized in that the probe is comprised of a receiving unit for the lamp, the light guide and the optical lenses, and in that the components of this optical axis are mounted fixed in place or displaceably arranged in the direction of the axis, and in that a measuring cylinder, preferably made of UV-transparent quartz glass, intersects with its central axis the optical axis at an angle of 90° and with the cylinder being directed perpendicularly upward, and in that the measuring cylinder is equipped with a piston, and the piston features sealing and cleaning lips, and in that the piston contains at least one through-bore for a reference beam and that this through-bore extends in the vertical plane of the optical axis, and in that the axes run parallel relative to each other, and in that the piston is moved by way of a motor via a drive rod, and in that the lamp is connected to the supply electronics and the light guide is connected to the detector, and in that the supply electronics, the detector, the motor and further components are connected to the evaluation unit, and in that the evaluation unit controls all internal processes of the buoy and forwards the data, if need be, to an external computer, and in that these data are forwarded via the data line, and in that this line is also used to supply the buoy with power.

BRIEF DESCRIPTION OF THE DRAWINGS

Subsequently, embodiments of the invention are described in more detail utilizing the drawings.

DESCRIPTION OF PREFERRED EMBODIMENTS OF THE INVENTION

Figure 1:
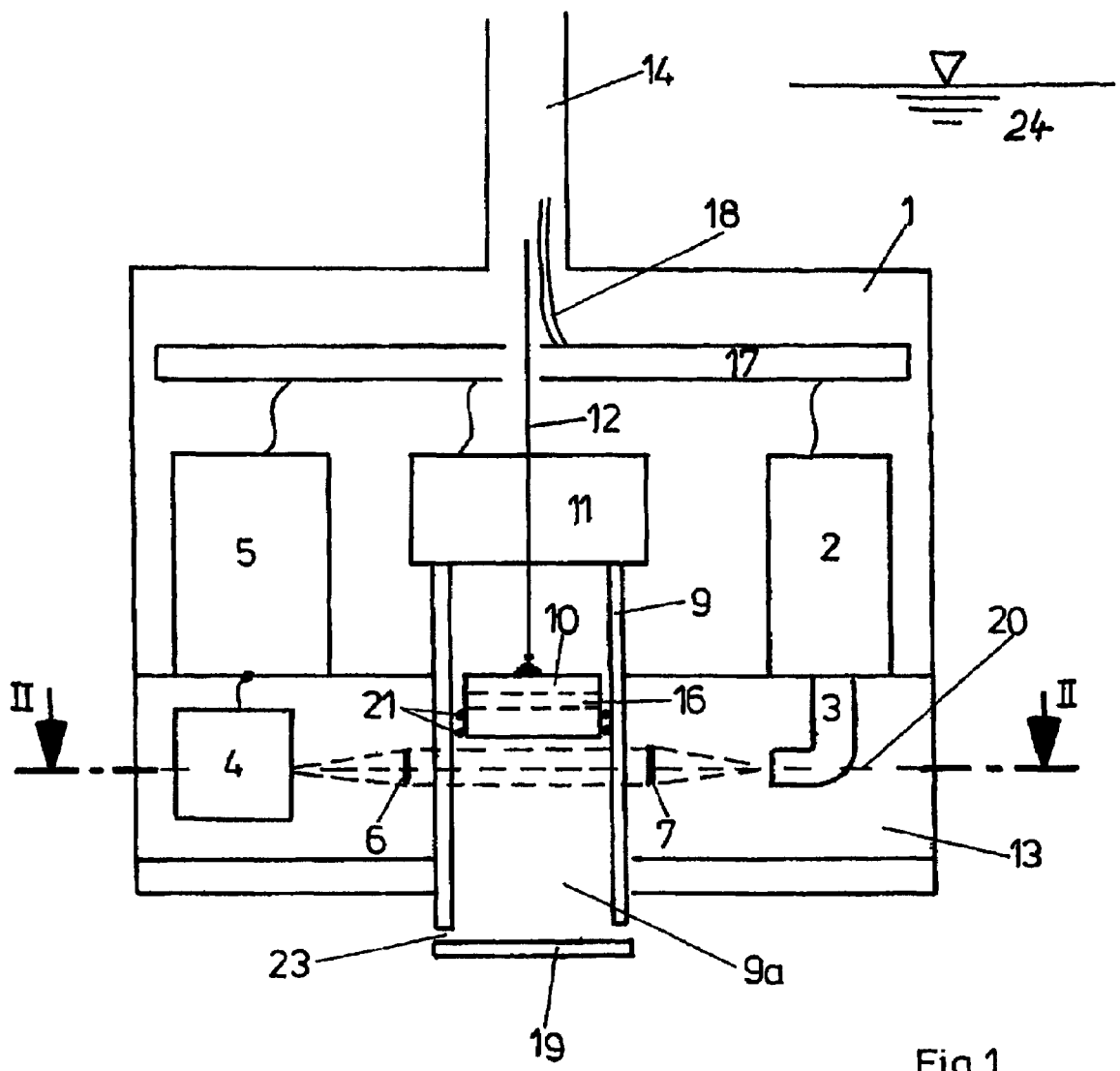
FIG. 1: a simplified depiction of an apparatus for the spectrometric "in situ" measurement with the measuring probe being represented in a longitudinal section.

A receiving unit 13 for the optical components is placed in the lower part of an essentially cylindrical probe 1. A lamp 4, a light guide 3 and optical lenses 6 and 7 are arranged with their optical centers in optical axis 20. For purposes of fine alignment, they can be displaceably arranged in the direction of the axis or mounted as fixed in place. The optical effect of lenses 6 and 7 can also be achieved with a corresponding cut of a measuring cylinder.

Lamp 4 is connected to a supply electronics 5, and light guide 3 is connected to optical detector 2. Measuring cylinder 9 is preferably manufactured of UV-resistant and UV-transparent quartz glass. Its cylinder axis intersects optical axis 20 at an angle of 90°. It has a diameter of between 5 and 30 mm.

A piston device 10, such as a piston or piston slide valve, is equipped with sealing and cleaning lips 21. Reference bore 16 for a reference beam extends in the vertical plane of optical axis 20 and parallel to the latter. Piston 10 is moved by means of motor 11 and via drive rod 12. The lower exit of measuring cylinder 9 features a floor piece 19 with integrated inlet and outlet openings 23. The lower entry of measuring cylinder 9 is equipped with a microscreen filter. The task of floor piece 19 consists in holding back any air bubbles that may rise. Openings 23 serve for filling and evacuating measuring cylinder 9.

An evaluation unit 17 is connected to detector 2, motor 11, supply electronics 5 and further components; and it controls all internal processes. Said unit is able to function as a temporary storage and can forward data to an external computer. Line 18 serves for the power supply and data transfer. Fastening pipe 14 is also used for lowering and lifting probe 1.

A measuring cycle occurs, for example, as follows: each measuring cycle starts with the evacuation of the measuring medium from internal chamber 9a of measuring cylinder 9. Piston 10 is lowered while simultaneously cleaning the internal walls of measuring cylinder 9 with its sealing and cleaning lips 21. During this process the medium is pressed through openings 23 and out of measuring cylinder 9. To fill measuring cylinder 9, piston 10, while being driven by motor 11, moves upward. When the reference bore 16 is congruent (coincides) with optical axis 20, lamp 4 blinks one or several times.

Lens 6 redirects the beams in such a way that they penetrate the interior of measuring cylinder 9, for the most part, as parallel beams. Then, lens 7 redirects these beams into the inlet of light guide 3. The bore axis is free of medium, which is why, when the beams pass through measuring cylinder 9 that is made of quartz glass, the extinction of the glass, including its opacity and contamination, is measured and serves as reference beam. If piston 10 exceeds the beam area of optical axis 20 when it is moved upward, lamp 4 blinks once again and measures extinction C of the glass cylinder (as above) as well as the specific total extinction module $E_{spez}$ in the total cross-section of the measuring piston.

The influence of possible opacity, discolorations and contaminations of the glass cylinder in the area of the light beam can therefore be compensated for based on a comparison of reference and measuring beams and using mathematical means. The mathematical relationship for each of the measured light waves is as follows:

| | |
|---|---|
| E1 = | L1*$E_{spez}$ + C |
| E2 = | L2*$E_{spez}$ + C |
| E1 = | measured extinction in path 1 |
| E2 = | measured extinction in path 2 |
| L1 = | length of measurement path (m) |
| L2 = | length of reference path (m) |
| $E_{spez}$ = | specific total extinction module of the medium (1/m) |
| C = | extinction of the glass cylinder due to discoloration, opacity and contamination (–) |

The solution is found with the usual mathematical methods.

For water types with minimal contamination it is possible to implement the reference measurement with distilled water in the measuring chamber 9a as well.

In an expansion of the method for measurements in the lagoon of a water treatment plant, piston 10 is lifted upward at such a slow speed that the activated sludge in the lower area of measuring cylinder 9 generates a suspension filter made of activated sludge resulting in the collection of a medium in the area of optical axis 20 that is, for the most part, free of solid matter. If the lower edge of piston 10 exceeds the upper range of the beam of rays of axis 20, the state of the medium as to its being free of solid matter is checked by way of a measurement of the absorption. With sufficient settling quality, the actual photometric measurement begins.

In a further supplementation of the method for measurements in the lagoon of a water treatment plant, piston 10 for filling the measuring cylinder is pulled upward at such a speed that any de-blending of sludge and measuring medium cannot occur, e.g., 0.5 to 2.0 cm per second. If the lower edge of piston 10 exceeds the upper range of the beam of rays of optical axis 20, the solid matter content of the activated sludge is measured. Thereafter, the settlement level of the medium-sludge blend is measured in second-intervals that are to be preset until a medium is achieved that is, for the most part, free of solid matter and after which time it is possible to initiate the actual photometric measurement.

With the measurement of the sedimentation profile, it is possible to determine the so-called sludge volume in ml/l. In conjunction with the previously established solid matter content g/l, a substitute value for the so-called sludge index is also available. The sludge index corresponds to sludge volume (ml/l)/solid matter content (g/l).

Figure 2:
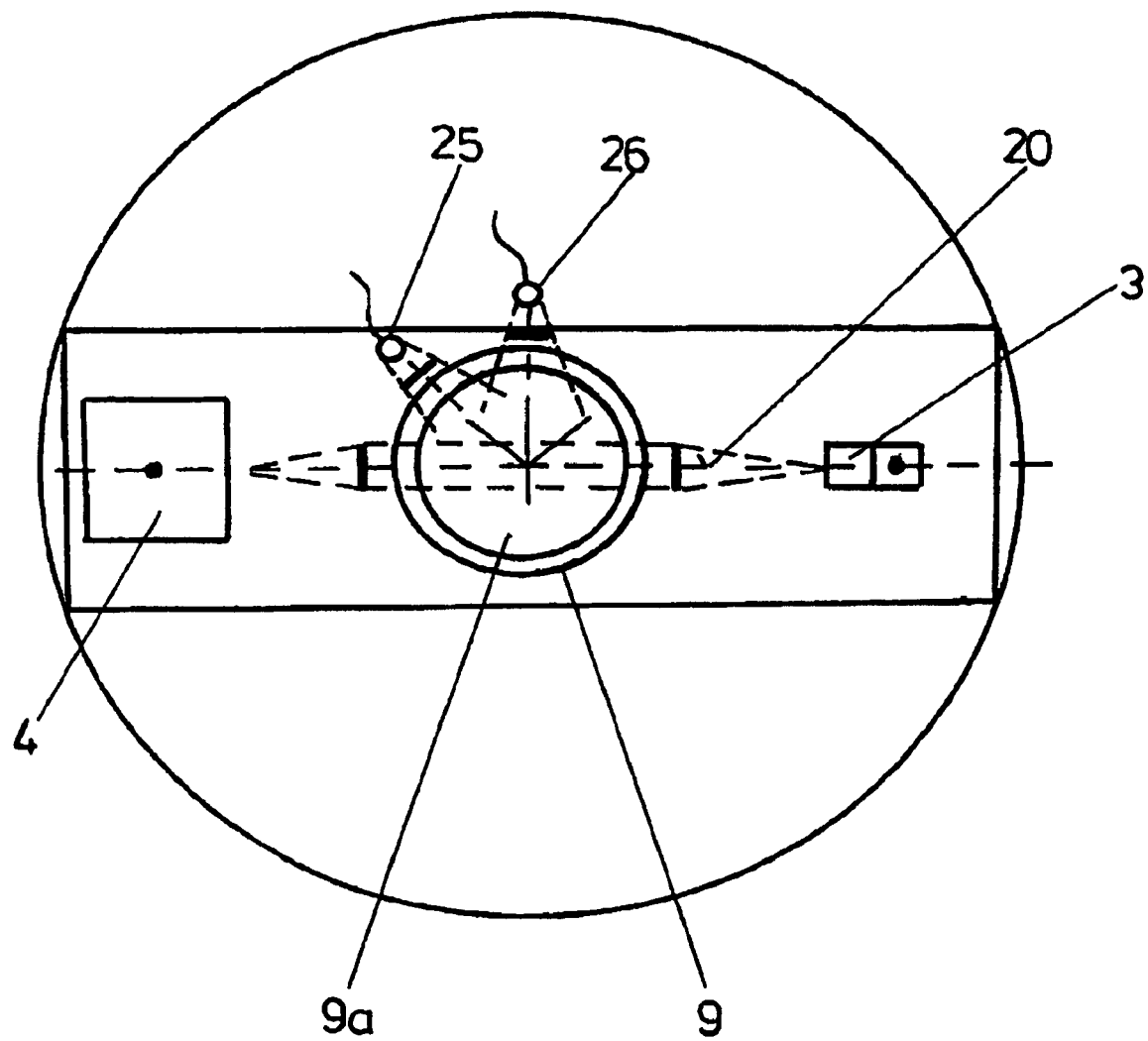
FIG. 2: a section along the line II-II in FIG. 1.

As shown in FIG. 2, it is possible to envision lateral photo detectors 25, 26 for the determination of the light scattering; they measure the light scattering at preset angles of, for example, 45° and/or 90° relative to the optical axis 20.

Figure 3:
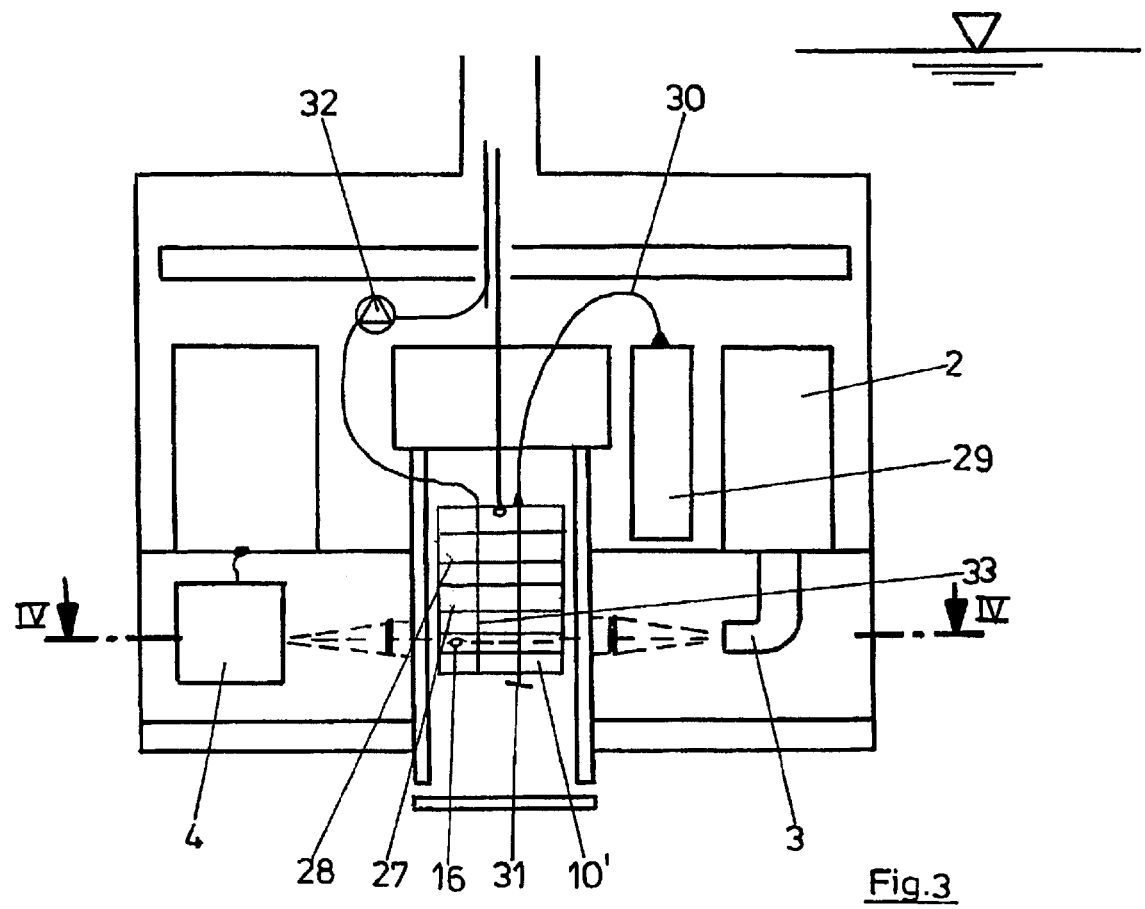
FIG. 3: a modified configuration of a photometric probe.
Figure 4:
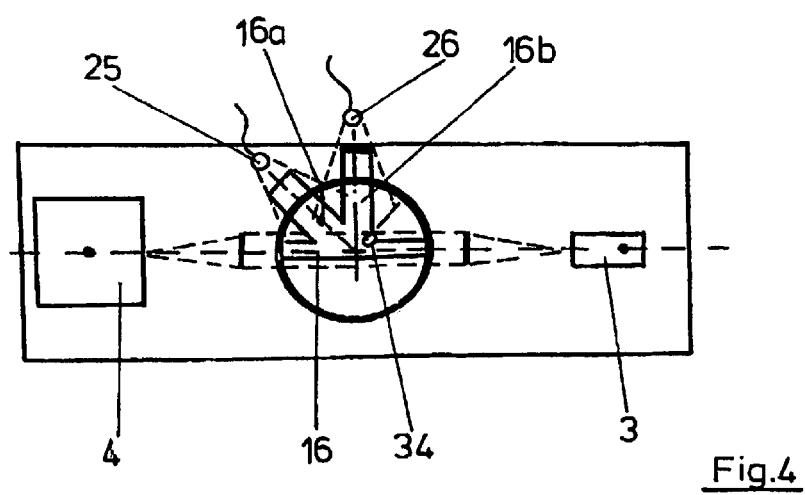
FIG. 4: a section along the line IV-IV in FIG. 3.

The configuration according to FIG. 3 and FIG. 4 differs from the previously described design essentially in that piston 10' has, in addition to bore 16, at least one further bore for the reference beam, for example axially offset further bore 27, 28, that can be filled for calibration purposes with different calibration liquids or calibrating materials, such as gels.

A stirring tool 31 for the purpose of achieving an intensive thorough-mixing of the fluid can be driven via motor 29 and flexible shaft 30. This is particularly useful if reagents are added by way of a reagent pump 32 and a flexible reagent line 33 opening into the interior of the cylinder.

FIG. 4 shows that reference bores 16a and 16b branch off from reference bore 16, which is used for calibrating the photo-detector 2; this way it is also possible to calibrate the scatter-light sensors 25 and 26. A diffuser 34, for example made of glass, can be eccentrically inserted into bore 16 to generate a defined scattering for calibration purposes.

The optical detector 2 can be a spectral photometer covering, with an associated light source 4, a wavelength range of approximately 190 to 800 nm for the spectrometry. For simple areas of application, however, using an LED as light source and a simple photo-diode as receiver may also make sense. Such a solution is easy to implement and very cost efficient. Laser diodes, in their capacity as strong monochromatic light sources, make sense as a solution for the detection of selected wavelengths. In a combination with a suitable photo-detector, it is possible to record very minimal concentrations. The use of infrared light, in particular of NIR, is indicated if substances are to be selectively detected from inside blends.

The invention claimed is:

1. A method for determining the content materials of a liquid medium using a light source and an optical detector arranged to define an optical beam path extending through a measuring chamber; wherein the light source directs at least one measuring beam along the optical beam path through the medium, and at least one reference beam along the optical beam path outside of the medium; wherein the medium is sucked into, and evacuated from, the measuring chamber by the displacement of a piston device within the measuring chamber; wherein the piston device cleans at least a portion of an internal surface of the measuring chamber disposed in the optical beam path as the piston is displaced within the measuring chamber; and wherein the spectrometric measurement is carried out when a lower edge of the piston device is congruent with upper edges of respective optical lenses disposed in the optical beam path, and the results of the reference beam and of the measuring beam are calculated for each wavelength or for individual areas of the spectrum in accordance with the mathematical relations:

$$E1 = L1 * E_{spez} + C$$

$$E2 = L2 * E_{spez} + C$$

wherein
E1=measured extinction in measuring beam
E2=measured extinction in reference beam
L1=length of measurement path
L2=length of reference path
$E_{spez}$=specific total extinction module of the medium
C=extinction of the cylinder due to discoloration, opacity and contamination.

2. The method according to claim 1 wherein the measuring chamber comprises a light-transparent cylinder, the inside surface of which is cleaned by the piston device.

3. The method according to claim 1, wherein the cylinder comprises glass.

4. The method according to claim 1 wherein the spectrometer is configured as a probe; the measuring chamber is configured as a cylinder; and the piston device includes external cleaning/sealing lips; when the piston device is raised within the cylinder, medium is sucked into the cylinder through an opening of a base of the probe that is immersed in the medium, and an inside wall of the cylinder is cleaned by the cleaning/sealing lips; when the piston device is lowered within the cylinder, the medium is expelled from the cylinder through the opening, and the inside wall is cleaned by the cleaning/sealing lips; the piston device including a reference passage which during piston displacement becomes coincident with the optical beam path, whereupon the reference beam is directed along the optical beam path and through the reference passage to perform a reference measurement; and wherein the measurement beam is directed along the optical beam path and through the medium to perform a measurement of the medium when the piston device has passed the optical beam path.

5. The method according to claim 1 wherein the reference beam constitutes a first reference beam, and further including directing a second reference beam along the optical beam path, and selecting an optimal reference beam from among the first and second reference beams.

6. The method according to claim 1 wherein activated sludge is contained in the medium; wherein an upward displacement of the piston for sucking the medium upwardly into the measuring chamber is performed at a speed slow enough to prevent sludge solids from collecting in the optical beam path during a measurement of the medium.

7. The method according to claim 1 wherein activated sludge is contained in the medium; wherein an upward displacement of the piston device for sucking the medium upwardly into the measuring chamber is performed at a speed for preventing a de-blending of the medium and sludge solids; when a lower edge of the piston device coincides with respective upper edge of optical lenses arranged in the optical beam path, a level of settling of the sludge-medium blend is optically measured in second-intervals for determining: the sludge dry solid matter, the sludge volume, and the sludge index; wherein after the medium in the optical beam path is substantially free of sludge solids, the measurement of the medium is performed.

8. The method according to claim 1 wherein the light beam from the light source is fanned and brought into focus in an essentially parallel beam by at least one optical lens disposed in the optical beam path.

9. The method according to claim 1 wherein the optical detector comprises a spectrometer.

10. A probe for determining the content materials of a liquid medium, comprising:
a measuring cylinder forming a measuring chamber and defining a vertical center axis;
a lamp for producing an optical beam directed along an optical beam path passing through the cylinder perpendicularly to the center axis, the optical beam path including optical lenses disposed therein;
a light guide for receiving the optical beam;
a photo-detector for receiving the optical beam from the light guide;
an evaluation unit operably connected to the lamp and the detector;
a piston device displaceable vertically within the cylinder for sucking-in medium upon being raised, and for expelling the medium upon being lowered, a through-passage extending through the piston device and arranged to become coincident with the optical beam path during vertical travel of the piston device within the cylinder, the piston device including a lower edge positioned congruent with upper edges of respective optical lenses disposed in the optical beam path during a spectrometric measurement, and external sealing/ cleaning lips arranged for cleaning at least a light-transparent portion of an internal surface of the cylinder disposed in the optical beam path as the piston is moved within the cylinder; and a motor operably connected to the piston device for effecting vertical movement thereof.

11. The probe according to claim 10 wherein the measuring cylinder includes a medium-conducting opening at a lower end thereof.

12. The probe according to claim 11 wherein the opening includes a micro-screen filter.

13. The probe according to claim 10 wherein the piston includes at least one additional through-passage for a reference beam.

14. The probe according to claim 10 wherein a diameter of the cylinder is between 5 and 30 mm.

15. The probe according to claim 10 wherein the measuring chamber comprises a glass cylinder.

16. The probe according to claim 10 wherein the photo-detector comprises a spectrometer.

17. The probe according to claim 10, wherein the piston device operates as a shutter by the positioning of the lower edge.

18. A probe for determining the content materials of a liquid medium, comprising:

a measuring cylinder forming a measuring chamber and defining a vertical center axis;

a lamp for producing an optical beam directed along an optical beam path passing through the cylinder perpendicularly to the center axis;

a light guide for receiving the optical beam;

a photo-detector for receiving the optical beam from the light guide;

an evaluation unit operably connected to the lamp and the detector;

a piston device displaceable vertically within the cylinder for sucking-in medium upon being raised, and for expelling the medium upon being lowered, a through-passage extending through the piston device and arranged to become coincident with the optical beam path during vertical travel of the piston device within the cylinder, the piston device including external sealing/cleaning lips arranged for cleaning at least a light-transparent portion of an internal surface of the cylinder disposed in the optical beam path as the piston is moved within the cylinder; and a motor operably connected to the piston device for effecting vertical movement thereof, wherein the piston includes at least one additional through-passage for a reference beam.

* * * * *